(12) United States Patent
Jubrail

(10) Patent No.: US 7,500,981 B1
(45) Date of Patent: Mar. 10, 2009

(54) EAR CLEANING DEVICE

(76) Inventor: Lucy Jubrail, 68965 Durango Rd., Cathedral City, CA (US) 92234

(*) Notice: Subject to any disclaimer, the term of this patent is extended or adjusted under 35 U.S.C. 154(b) by 548 days.

(21) Appl. No.: 11/156,971

(22) Filed: Jun. 21, 2005

(51) Int. Cl.
*A61F 9/00* (2006.01)
(52) U.S. Cl. ..................................... 606/162
(58) Field of Classification Search ................ 606/162; 600/200; 81/439; 604/1, 2; 206/363, 370, 206/438
See application file for complete search history.

(56) References Cited

U.S. PATENT DOCUMENTS

| 4,901,391 | A | | 2/1990 | Athalye |
| 5,065,498 | A | * | 11/1991 | McKenzie ................ 483/57 |
| 5,209,692 | A | | 5/1993 | Coleman et al. |
| D356,213 | S | | 3/1995 | Chaves |
| 5,536,054 | A | | 7/1996 | Liaw |
| 5,632,756 | A | | 5/1997 | Kruglick |
| 5,715,850 | A | | 2/1998 | Markgraaf |
| 5,893,685 | A | * | 4/1999 | Olson et al. ................ 408/35 |
| 5,931,845 | A | * | 8/1999 | Amyette .................... 606/162 |
| 6,171,312 | B1 | * | 1/2001 | Beaty ........................ 606/80 |
| 6,187,021 | B1 | * | 2/2001 | Wim ........................ 606/162 |
| 6,517,511 | B2 | * | 2/2003 | Yao ............................ 604/35 |
| 6,601,483 | B2 | * | 8/2003 | Wannop ..................... 81/490 |
| 6,607,041 | B2 | * | 8/2003 | Suzuki et al. ............... 173/4 |
| 6,699,178 | B1 | * | 3/2004 | Koda ......................... 600/104 |
| 6,923,760 | B2 | * | 8/2005 | Koda et al. ................ 600/200 |
| 2004/0065177 | A1 | * | 4/2004 | Wannop .................... 81/177.4 |
| 2004/0249244 | A1 | * | 12/2004 | Koda et al. ................ 600/160 |

FOREIGN PATENT DOCUMENTS

WO        WO/94/04106        *  3/1994

* cited by examiner

*Primary Examiner*—Julian W Woo
*Assistant Examiner*—Jing Ou

(57) ABSTRACT

A device for cleaning a user's ear includes a hand held appliance with an attached cleaning tool. A first mechanism provides motion to the cleaning tool, a second is included to store one or more cleaning tools within the appliance, and a third mechanism is provided for automatically replacing the attached cleaning tool with another cleaning tool stored within the appliance. A charging stand for holding the device between uses is also included. Such a charging stand is connected to an active power source via a power cord.

1 Claim, 3 Drawing Sheets

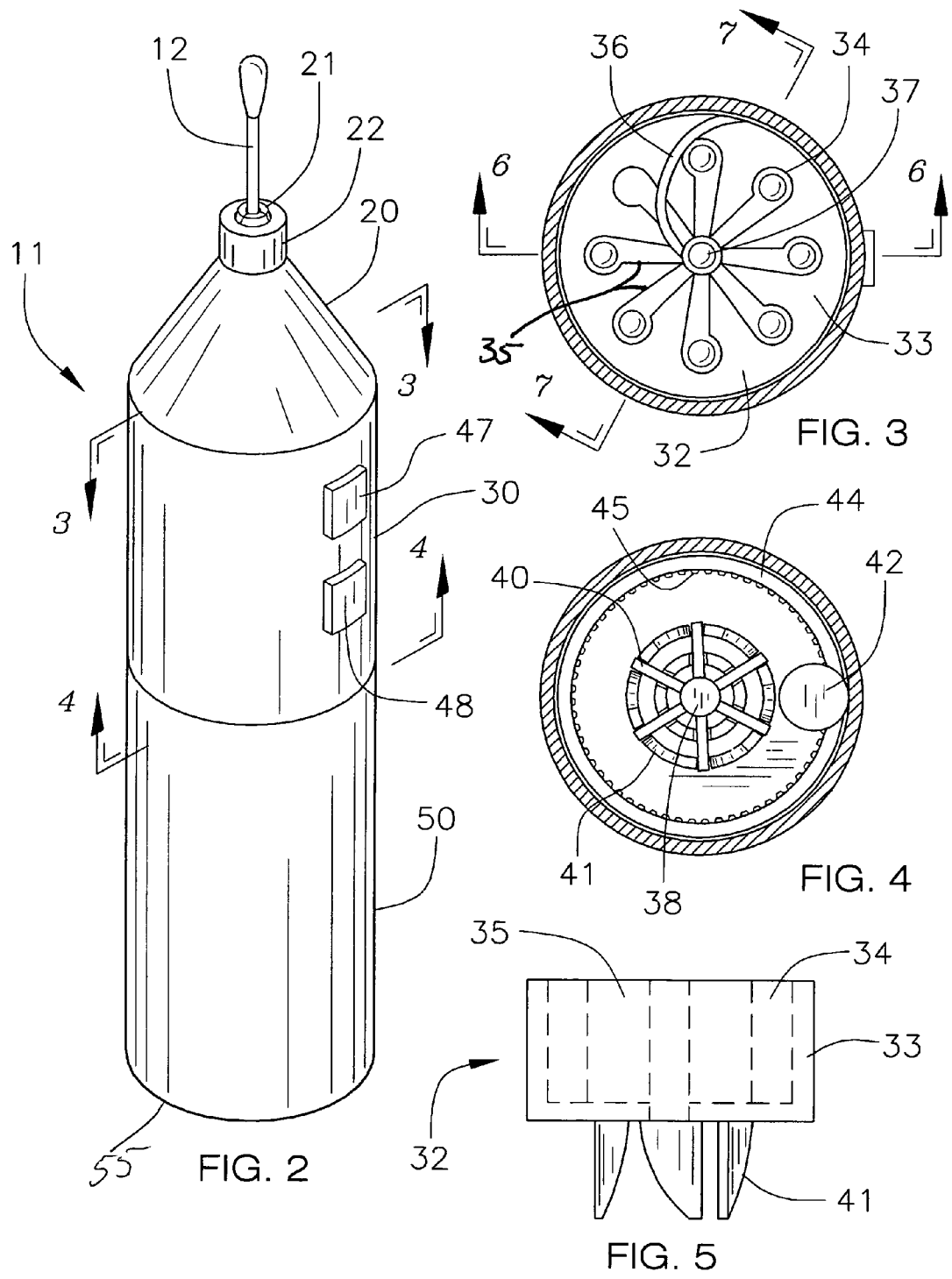

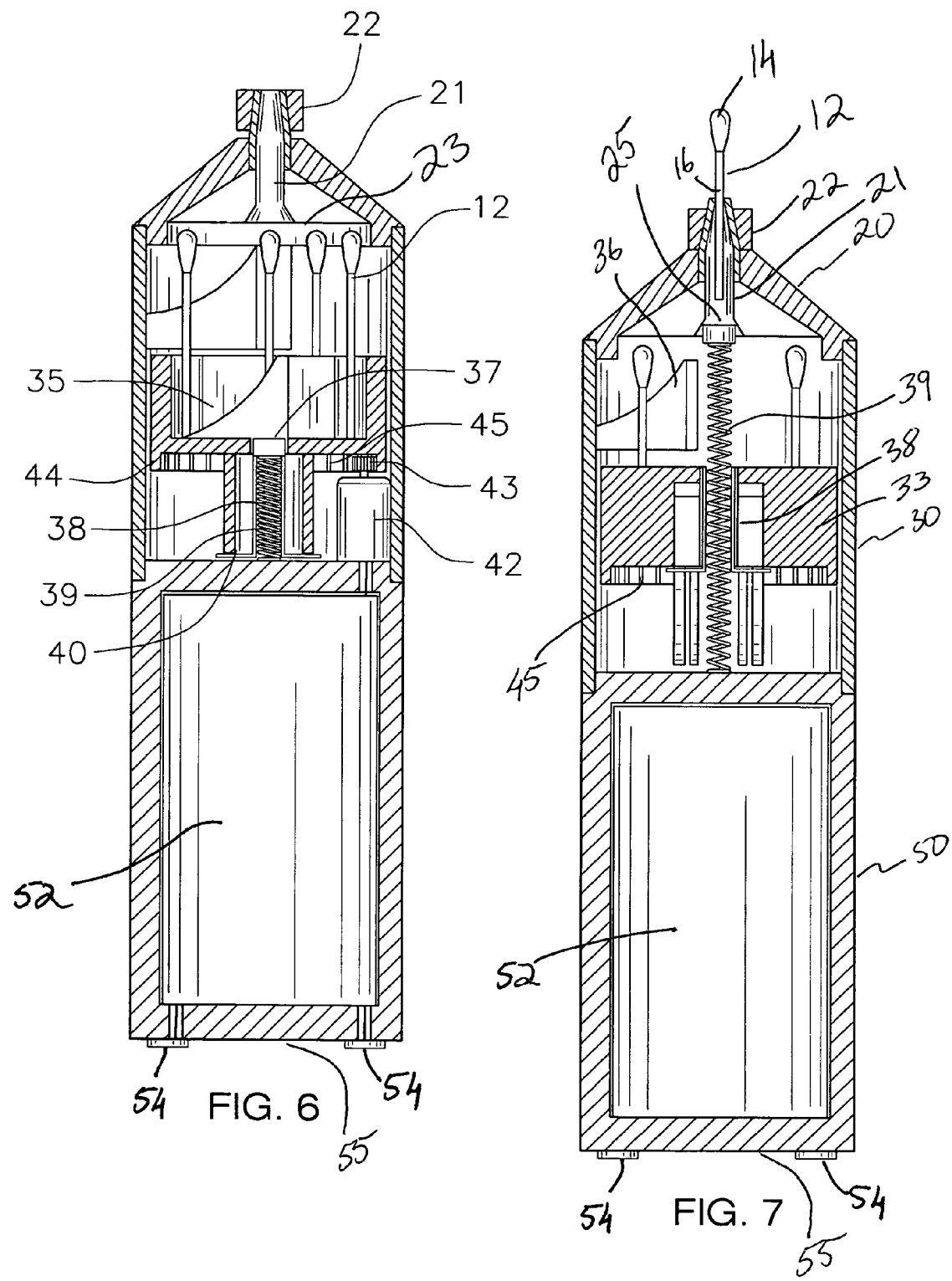

EAR CLEANING DEVICE

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to an instrument for removal of cerumen (ear wax) from a person's ear and, more particularly, to a new device that features a mechanism of actively moving the cerumen removal element (cleaning tool) and a mechanism for storing, disposing and deploying subsequent clean cerumen removal elements.

2. Prior Art

When wax build-up is in an ear canal a person may try to remove the wax with a cotton tipped applicator. The person may get most of the wax out, but the wax is usually pushed farther down into the ear canal, where it becomes impacted. Adequate examination of the eardrum is impossible. A quick, painless removal of the wax by a doctor becomes difficult and frustrating. Although wax rarely causes deafness, it must be removed. If the doctor cannot remove the wax deftly the first time with a looped curette scoop, then the wax in the ear canal must be washed out. This ear enema is frightening to the person and time consuming for the doctor.

Numerous tubular ear passage manipulators have been provided in the prior art that are adapted to extract cerumen, to massage and to generally cleanse the tubular passage of the ear. These devices generally consist of an elongated element with a cleansing member at one tip thereof that can be safely fitted into the ear.

A drawback of such ear cleaning devices is that no means is provided for cleaning the outer regions of the ear canal so that, even after cleaning using that device, wax or other dirt can remain at the entrance to the ear canal, or a short distance inwardly therefrom, which may be unsightly. Another disadvantage is the need to manually operate such a cleaning device. Many people do not perform this task properly and are at risk of injuring the structure of their inner ear, which could lead to deafness. The previously mentioned cleaning devices also continuously use only one cleaning member, which is not sanitary and limits the use of the device to only one person.

Accordingly, a need remains for an ear cleaning device in order to overcome the above-noted shortcomings. The present invention satisfies such a need by providing an ear cleaning device that is easy, effective and convenient to use, and also provides improved health benefits over previous examples in the prior art. Such a device can conveniently be offered in both adult and pediatric versions for use by all people. The automated ear cleaning device allows for more effective cleaning of the ears, leading to more accurate diagnosis of ear ailments, while also reducing the risk of hearing loss and equilibrium problems related to excessive cerumen accumulation. Such a device is appreciated by adult, parents, health professionals, and those with physical limitations that prevent them from manually swabbing their ears.

BRIEF SUMMARY OF THE INVENTION

In view of the foregoing background, it is therefore an object of the present invention to provide an ear cleaning apparatus. These and other objects, features, and advantages of the invention are provided by a device that provides a user with an instrument that holds a disposable cerumen removal element which can be activated to move thus increasing the elements effectiveness in removing cerumen from a person's ear.

Additionally this instrument will store a number of cerumen-removing elements and a method of automatically replacing the held cerumen-removing element with one of the stored cerumen-removing elements automatically.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 2 is a perspective view of the device shown in FIG. 1;

FIG. 3 is a cross-sectional view of the device shown in FIG. 2, taken along line 3-3;

FIG. 4 is a cross-sectional view of the device shown in FIG. 2, taken along line 4-4;

FIG. 5 is a side-elevational view of the cam release element of the device shown in FIG. 2;

FIG. 6 is a cross-sectional view of the device shown in FIG. 3, taken along line 6-6; and FIG. 7 is a cross-sectional view of the device shown in FIG. 3, taken along line 7-7.

DETAILED DESCRIPTION OF THE INVENTION

Figure 1:
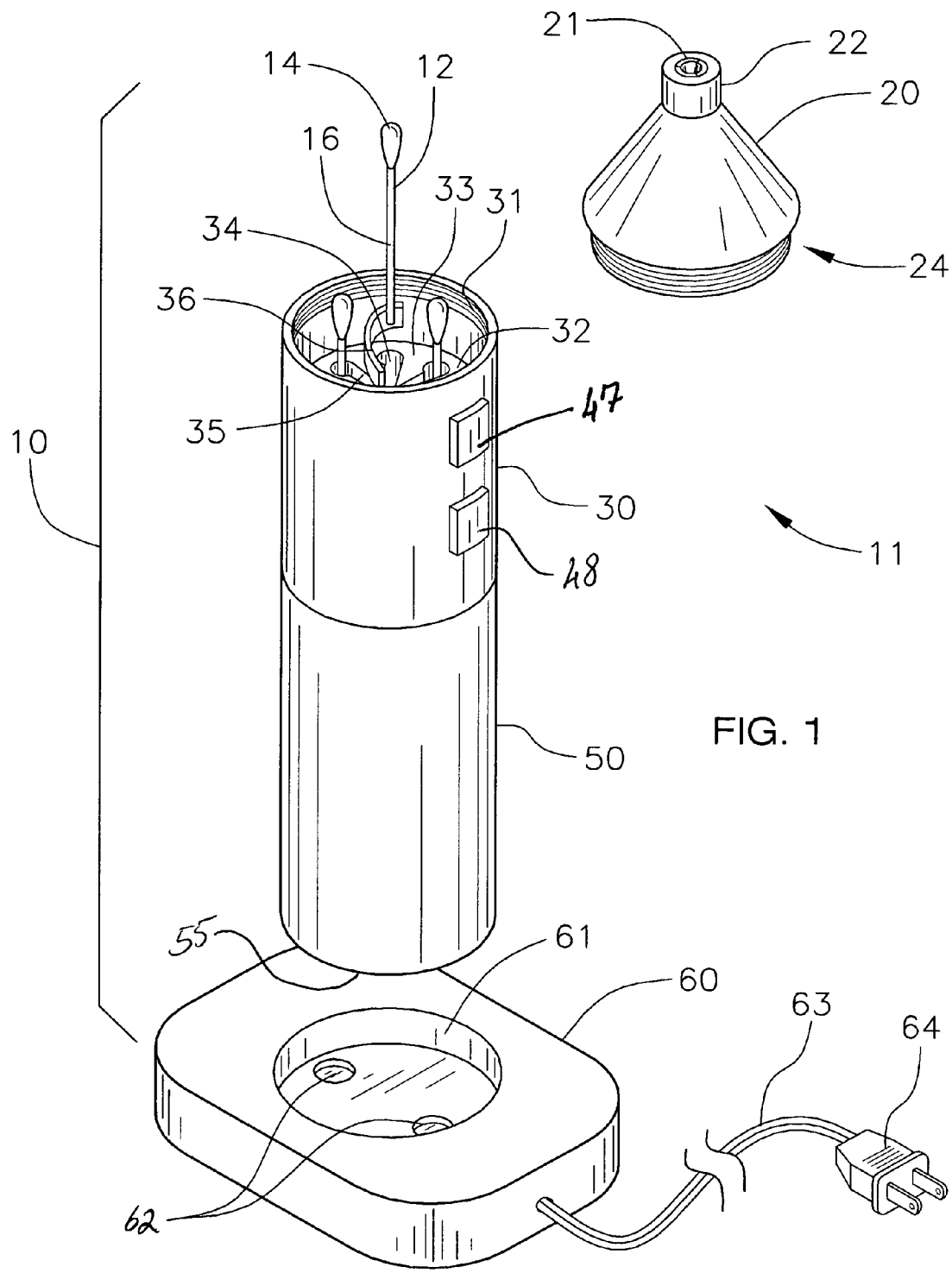
FIG. 1 is a partially exploded perspective view showing an ear cleaning device, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The device of this invention is referred to generally in FIGS. 1-7 by the reference numeral 10 and is intended to provide an ear cleaning device. It should be understood that the device 10 may also be used clean the ears of young children and should not be limited in use to only adults.

Referring initially to FIGS. 1 through 7, the device 10 includes a hand held appliance 11 and a charging stand 60 for holding the appliance 11 between uses. The appliance 11 is comprised of a top section 20 incorporating a loading channel 21 for passing cerumen removal elements 12 from the staged position 37 of the middle section 30 to the position of use 25 in the top section 20. The cerumen removal element 12 is depicted in the illustration as a cotton swab with a cleaning surface 14 and a shaft 16 although the invention is not so limited. For example, the cerumen removal instrument 12 may also be a shaft 16 with a banded cage or other shape made of a resiliently deformable soft plug of cleaning material as cited in the prior art. The cerumen removal element will hereafter be referred to as "cleaning tool 12". The gripping collar 22 is designed to hold firm the cleaning tool 12 in the position of use and is designed to transition from a release mode to a gripping mode securing the shaft 16 of the cleaning tool 12 while in use and confer to the cleaning tool 12 the motion generated by the motion providing mechanism 23 (described herein below).

Referring to FIGS. 1, 2, 6 and 7, the gripping collar 22 may be a series of radial grip surfaces held in place by a rigid collar acting as a wedge against each individual grip. A spring bias may provide force to the collar 22 and thus put positive pressure against the grip assembly and thus to the center channel 21. Other methods of gripping around a central channel 21 are also anticipated. For example, a chuck design as is known and practiced in drill assemblies for holding drill bits. Or an offset cam that would press into the channel as is known in telescopic pole or handle devices. The gripping collar 22 may be manually actuated or automatically controlled by a device such as a screw push motor, solenoid or magnetic lock ring.

Referring to FIG. 6, a mechanism for providing motion 23 may also be located in the top section and directly connected to the gripping collar 22. The motion providing mechanism 23 illustrated in the drawings is depicted as a piezoelectric vibrator although the invention is not so limited. For example, the motion providing mechanism 23 may also be comprised of a motor with offset weight producing a rotary vibration, a motor with geared attachment to provide a rotation of the cleaning tool 12 or a motor with crank attachment to the gripping collar 22 to produce a wobbling motion. The motion providing mechanism 23 would be powered by the battery 52 and controlled through the On/Off control 48.

Referring to FIG. 1, the top section 20 may be connected to the middle section 30 by the coupling of the top section coupling system 24 to the middle section coupling system 31. In FIG. 1, the top section coupling system 24 is shown to have a threaded lower section and the middle section coupling system 31 is shown to have a threaded upper section that can effectively be threadably engaged with the threaded section of the top section coupling system 24. Of course, alternate coupling systems may be employed as is anticipated by the prior art. For example, a latch mechanism may be used to secure the top section 20 to the middle section 30 with a release button provided on the outer surface of the middle section 30 to allow for effectively disengaging the top 20 and middle 30 sections.

Referring to FIGS. 1, 2, 6 and 7, the device 10 further includes a mechanism for storing cleaning tools including a magazine assembly 32 that has an annular magazine 33 positioned within the middle section 30. Such a magazine 33 is rotatable about a central vertical axis that is vertically aligned above the staging area 37. The magazine 33 includes a plurality of tool holding cavities 34 that are essential for holding a predetermined number of cleaning tools 12. A plurality of connecting grooves 35 extend inwardly from the plurality of tool holding cavities 34 towards the center of the magazine 33. The magazine assembly 32 also includes an arcuate shaped positional guide 36 that has opposed end portions. One of the end portions is attached to the interior surface of the middle section 30 above the magazine 33 and the other end portion is located adjacent to the center of the magazine 33, respectively.

Referring to FIGS. 1, 6, and 7, as the magazine 33 rotates about the central axis, a cleaning tool 12 positioned in the tool holding cavity 34 engages one end portion of the positional guide 36 which is vital for causing the cleaning tool 12 to move along the respective connecting groove 35 of the tool holding cavity 34. As rotation of the magazine 33 continues, the cleaning tool 12 becomes horizontally displaced along the connecting groove 35 towards the center of the magazine 33, and subsequently the staging area 37. Of course, the staged area 37 may be located on the outside of the edge of the magazine 33 similar to the breach of a radial magazine feed firearm or coaxial to the tool holding cavities similar to the magazine of a revolver.

Referring to FIGS. 4 and 6, a magazine motor 42 is located beneath the magazine assembly 32 and is mechanically coupled to the magazine assembly 32 by a drive gear 43. The bottom of the magazine assembly 32 is rimmed with an engaging ring 44 lined with gear teeth 45 that mesh with the drive gear 43.

Referring to FIGS. 4 and 5, a cam 41 is also disposed on the underside of the magazine assembly. The cam 41 controls the movement of the push arm 38 by its connection to the push arm tabs 40 located at the bottom end of the push arm 38. As the cam 41 turns as part of the magazine assembly 32 the cam 41 forces the push arm 38 down against the spring bias of the push arm springs 39 via cam motion on the push arm tabs 40 to a first position that would allow the motion of the magazine assembly 32 to place a cleaning tool 12 into the staged position 37.

Further rotation of the magazine assembly 32 would move the cam 41 to a position where it would release the push arm 38 and the cleaning tool 12 placed in the staged position to move up using the spring bias of the compressed push arm spring 39 into a second position. This second position is achieved when the top of the push arm 38 is in contact with the bottom of the loading channel 21 and the push arm spring 39 is relatively decompressed. In this second position the cleaning tool 12 would be in position to be gripped by the gripping collar 22. The cam 41 would retract and subsequently release the push arm 38 through the rotation of the magazine 33.

Referring to FIGS. 1 and 2, on the exterior of the middle section 30 there may be controls for controlling the function of the appliance 11. One such control would be the On/Off control 48 for activating or deactivating the motion of the cleaning tool 12 by providing or cutting power to the motion actuating system 23. Another such control may be the reload control 47 for replacing the cleaning tool 12 in the gripping collar 22 with a new cleaning tool 12 from the magazine 33.

Other anticipated controls may include a control for releasing the cleaning tool 12 without replacing it with another, a motion speed control managing the output or speed of the motion providing mechanism, a battery cycling control and etcetera.

Referring to FIGS. 1, 6, and 7, the lower section 50 may include a rechargeable battery 52 for operating the inherent motors of the appliance 11. The battery 52 would be electrically coupled to the magazine motor 42, the motion actuating system 23, the controls 47, 48 and possibly the gripping collar 22. It is anticipated that the appliance 11 may include other elements requiring access to electrical power such as indicators e.g. battery charge indicator, display device etc. or other outputs such as audio speaker or buzzer e.g. warning alarm, battery low tone generator. The battery 52 may have charging contacts 54 located on the exterior of the appliance 11 for coupling with a charging stand 60. The illustrations depict exterior flat contact pads 54 although the invention is not so limited. For example, the electrical connection may take the form of a variety of DC connector plugs or pin connectors with or without guides.

Referring to FIG. 1, the charging stand 60 may be designed with a recessive cavity 61 to hold the ear cleaning device 10. This cavity would in case conform to the shape of the mating end 55 of the lower section 50 so that the charging contacts 54 on the bottom of the appliance 11 would mate with the electrical contacts 62 of the charge stand 60. The receiving cavity 61 would in that case correspond to the design of the mating end 55 of the lower section 50 so that it could hold the appliance 11 firmly in both a vertical and horizontal orientation.

Still referring to FIG. 1, the electrical contacts 62 may be electrically coupled to an AC to DC transformer with appropriate charging circuitry for recharging the battery 52. The transformer itself may be located in the charging stand 60 or located in the outlet connector 64 generally referred to in the industry as a wall wart. The charging stand would be connected to either AC power in the case of the transformer located in the charging stand 60 or to DC power if the transformer were located in the outlet connector via an electrical cord 63.

Referring to FIGS. 1, 2, 6, and 7, the exterior of the appliance 11 may be relatively cylindrical in shape and would act as the handle for the use of the appliance 11. It is anticipated that the exterior could be contoured with gripping features or with applied gripping material. In use the ear cleaning device 10 is used to remove cerumen from the user's ear. It performs this function when a cleaning tool 12 is locked in the position of use by the gripping collar 22 so that the end of the cleaning tool 12 can make contact with the area to be cleaned. By triggering the On/Off control 48 the motion providing mechanism 23 would be activated and would produce movement to the gripping collar 22 that would be transmitted to the end of the cleaning tool 12. This motion would assist the cleaning capability of the cleaning tool 12 by providing a scrubbing action of the cleaning surface. The portable configuration of the appliance 11 would allow the user to direct the cleaning surface of the cleaning tool 12 to the locations in the ear.

Referring to FIGS. 1-7, when the user triggered the reload control 47 a series of actions would occur in the following order. First, the gripping collar 22 would retract thus releasing the cleaning tool 12 currently in the position of use. The push arm 38 would be in the first position with a cleaning tool 12 in the staged position 37 with the push spring 39 compressed. The magazine motor 42 would activate and start to rotate the magazine assembly 32 which would release the push arm 38 by dispensing the push arm tabs 40. The cleaning tool 12 would be propelled up through the loading channel 21 by the push arm 38. The push arm 38 would provide the motion as the push arm tabs 40 release from the cam 41 and use the spring bias to move the push arm 38 to the second position.

Still referring to FIGS. 1-7, the cleaning tool 12 would now be in the position of use and the gripping collar would be locked around the shaft 16 of the cleaning tool 12. As the magazine motor 42 continues to turn the magazine assembly all of the cleaning tools 12 located in the holding cavities 34 would advance and one cleaning tool 12 would engage the positional guide 36. The rotation of the magazine assembly would steer the cleaning tool 12 through the engagement with the positional guide 36 from the tool holding cavity 34 through the connecting groove 35 and into the staged position 37. Concurrently, with the loading of the cleaning tool 12, the rotation of the magazine assembly 32 would also engage the cam 41 against the push arm cam tabs 40 forcing the push arm 38 down into the first position and thus compress the push arm spring 39. The motor 42 would then deactivate, leaving the reloading system in the first position and ready to perform the reloading function again.

Referring to FIG. 1, the appliance 11 would be stored between uses in a charging stand 60 that could sit on a surface or be mounted on a wall. The appliance 11 would nest in the charge stand 60 by engaging the mating end 55 of the lower section 50 into the receiving cavity 61 of the charging stand 60. The tension of the mating contact would be sufficient to hold the appliance 11 in a horizontal position. The charge stand 60 would provide an electrical connection to the appliance 11 via charging contacts 54 on the mating end of the appliance 11 and electrical contacts 62 in the receiving cavity 61 of the charge stand 60. The charge stand 60 would be connected to an active power source via a power cord 63.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A device for cleaning a user's ears, said device comprising:
   a plurality of cleaning tools;
   a hand-held appliance and a charging stand for holding the appliance between uses, said appliance comprising
      a top section and a middle section removably coupled thereto, said top section having a loading channel for passing said cleaning tools from a staged position to a position of use in said top section,
      a gripping collar for holding one of said cleaning tool in the position of use,
      a mechanism for storing said cleaning tools, said storing mechanism comprising a magazine assembly having an annular magazine positioned within said middle section; said magazine being rotatable about a central vertical axis that is vertically aligned above said staged position, said magazine including a plurality of tool holding cavities, said tool holding cavities having a plurality of connecting grooves extending inwardly therefrom and towards a center of said magazine, said magazine assembly further including an arcuate shaped positional guide that has opposed end portions attached to an interior surface of said middle section above said magazine and located adjacent to the center of said magazine respectively;

wherein one of said cleaning tools is positioned in an associated one of said tool holding cavities and engages one of said end portions of said positional guide;

wherein rotation of said magazine causes said one cleaning tool to become horizontally displaced along an associated one of said connecting grooves towards the center of said magazine and subsequently the staged position, a staging area being located on an outside of an edge of said magazine;

a magazine motor located beneath said magazine assembly and mechanically coupled to said magazine assembly by a drive gear, a bottom of said magazine assembly being rimmed with an engaging ring lined with gear teeth that mesh with said drive gear;

a push arm having push arm tabs connected thereto and further having a push arm spring connected to said loading channel;

a cam disposed on an underside of said magazine assembly, said cam being connected to said push arm tabs for controlling movement of said push arm, wherein said cam turns as part of said magazine assembly and thereby forces said push arm down against said push arm spring via cam motion on said push arm tabs to a first position that allows motion of said magazine assembly to place said one cleaning tool into the staged position, wherein further rotation of said magazine assembly moves said cam to a position that releases said push arm and said one cleaning tool upwardly from the staged position to a second position, said second position being achieved when a top of said push arm is in contact with a bottom of said loading channel and said push arm spring is relatively decompressed respectively.

* * * * *